United States Patent
Ueda et al.

(10) Patent No.: US 10,561,375 B2
(45) Date of Patent: Feb. 18, 2020

(54) PULSE PHOTOMETER AND METHOD FOR EVALUATING RELIABILITY OF CALCULATED VALUE OF BLOOD LIGHT ABSORBER CONCENTRATION

(71) Applicant: NIHON KOHDEN CORPORATION, Shinjuku-ku, Tokyo (JP)

(72) Inventors: Yoshinori Ueda, Tokyo (JP); Teiji Ukawa, Tokyo (JP); Kazumasa Ito, Tokyo (JP); Hideki Fujisaki, Tokyo (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 482 days.

(21) Appl. No.: 15/248,489

(22) Filed: Aug. 26, 2016

(65) Prior Publication Data
US 2017/0055919 A1   Mar. 2, 2017

(30) Foreign Application Priority Data

Aug. 31, 2015 (JP) .................. 2015-170785
Jun. 9, 2016 (JP) .................. 2016-115721

(51) Int. Cl.
*A61B 5/1455* (2006.01)
*A61B 5/0205* (2006.01)
(Continued)

(52) U.S. Cl.
CPC .......... *A61B 5/7282* (2013.01); *A61B 5/0205* (2013.01); *A61B 5/14546* (2013.01);
(Continued)

(58) Field of Classification Search
CPC .............. A61B 5/0205; A61B 5/02433; A61B 5/14546; A61B 5/14551; A61B 5/14552; A61B 5/7221; A61B 5/7282
See application file for complete search history.

(56) References Cited

U.S. PATENT DOCUMENTS 3,638,640 A * 2/1972 Shaw ................. A61B 5/14552
                                                    600/323
4,714,341 A   12/1987 Hamaguri et al.
(Continued)

FOREIGN PATENT DOCUMENTS

| JP | 4196209 B2 | 12/2008 |
| JP | 4865737 B2 | 2/2012 |
| WO | 02/28274 A1 | 4/2002 |

OTHER PUBLICATIONS

Mendelson, "Pulse Oximetry", Wiley Encyclopedia of Biomedical Engineering, 2006.*
(Continued)

*Primary Examiner* — Eric F Winakur
(74) *Attorney, Agent, or Firm* — Sughrue Mion, PLLC

(57) ABSTRACT

A pulse photometer includes: a first variation acquirer acquiring a first variation corresponding to a light attenuation variation of a first light beam due to pulsation of blood in a subject based on a first intensity signal corresponding to an intensity of the first light beam transmitted through or reflected from a body of the subject and having a first wavelength; a second variation acquirer acquiring a second variation; a third variation acquirer acquiring a third variation; a concentration calculator calculating a blood light absorber concentration based on the first variation and the second variation; an estimated value calculator calculating an estimated value of the third variation based on the first variation and the second variation; and an evaluator evaluating reliability of a calculated value of the blood light absorber concentration based on the third variation and the estimated value.

16 Claims, 2 Drawing Sheets

(51) Int. Cl.
*A61B 5/00* (2006.01)
*A61B 5/145* (2006.01)
*A61B 5/024* (2006.01)

(52) U.S. Cl.
CPC ...... *A61B 5/14551* (2013.01); *A61B 5/14552* (2013.01); *A61B 5/7221* (2013.01); *A61B 5/02433* (2013.01)

(56) References Cited

U.S. PATENT DOCUMENTS

| | | | |
|---|---|---|---|
| 5,413,100 | A | 5/1995 | Barthelemy et al. |
| 5,782,756 | A | 7/1998 | Mannheimer |
| 6,801,799 | B2 * | 10/2004 | Mendelson ........ A61B 5/14552 600/322 |
| 2004/0267140 | A1 | 12/2004 | Ito et al. |
| 2006/0211925 | A1 | 9/2006 | Lamego et al. |
| 2008/0221463 | A1 * | 9/2008 | Baker ................ A61B 5/02416 600/500 |
| 2009/0318787 | A1 * | 12/2009 | Aoyagi ................ A61B 5/1455 600/323 |

OTHER PUBLICATIONS

Suzaki et al., "Noninvasive measurement of total hemoglobin and hemoglobin derivatives using multi-wavelength pulse spectrophotometry", Conf Proc IEEE Eng Med Biol Soc, 2006; 1: pp. 799-802.*

Barker et al., "The effect of carbon monoxide inhalation on pulse oximetry and transcutaneous P02", Anesthesiology 66, pp. 677-679, 1987.*

Nogawa et al. New Hybrid Reflectance Optical Pulse Oximetry Sensor for Lower Oxygen Saturation Measurement and for Broader Clinical Application, Proc. SPIE 2976, Jun. 16, 1997.*

Wukitsch et al., "Pulse Oximetry: Analysis of Theory, Technology, and Practice", Little, Brown, and Co., pp. 290-301, 1988 (Year: 1988).*

Communication dated Jan. 20, 2017 issued by the European Patent Office in counterpart European Patent Application No. 16186149.7.

* cited by examiner

PULSE PHOTOMETER AND METHOD FOR EVALUATING RELIABILITY OF CALCULATED VALUE OF BLOOD LIGHT ABSORBER CONCENTRATION

CROSS-REFERENCE TO RELATED APPLICATION(S)

This application is based upon and claims the benefit of priority from prior Japanese patent application No. 2015-170785, filed on Aug. 31, 2015, and Japanese patent application No. 2016-115721, filed on Jun. 9, 2016, the entire contents of which are incorporated herein by reference.

BACKGROUND

The presently disclosed subject matter relates to a pulse photometer, and also to a method for evaluating the reliability of a calculated value of the blood light absorber concentration.

A pulse photometer is an apparatus which calculates the blood light absorber concentration of the subject. Specifically, the living tissue of the subject is irradiated with light beams at a plurality of wavelengths which have different ratios of the blood light absorbances depending on the blood light absorber concentration. The intensities of the light beams at the wavelengths transmitted through or reflected from the living tissue are detected. The intensities at the wavelengths are changed in accordance with the pulsation of the blood in the subject. Therefore, temporal changes of the intensities at the wavelengths due to the pulsation are acquired in the form of a pulse wave signal. The amplitudes of pulse wave signals with respect to waveforms correspond to light attenuation variations with respect to the waveforms, respectively. The blood light absorber concentration is calculated based on a ratio of light attenuation variations with respect to waveforms (for example, see Japanese Patent No. 4,196,209).

As an example of the blood light absorber concentration, known is the arterial oxygen saturation (hereinafter, referred to as the SaO2) which is used as an index of blood oxygenation. In order to obtain the value of the SaO2, an invasive measurement must be performed. Therefore, the transcutaneous arterial oxygen saturation (hereinafter, referred to as the SpO2) which can be non-invasively calculated is widely used as the index. The SpO2 is calculated by a pulse oximeter which is an example of a pulse photometer.

Techniques for evaluating the reliability of a calculated value which is obtained as described above are available. In the technique disclosed in Japanese Patent No. 4,865,737, for examples, a calculated value is compared with a data value which is previously acquired in a predetermined measurement environment, and the reliability of the calculated value is evaluated in accordance with the difference between the values.

SUMMARY

The presently disclosed subject matter may provide an apparatus and a method to improve the accuracy of reliability evaluation for a blood light absorber concentration which is non-invasively calculated.

There may be provided a pulse photometer comprising: a first variation acquirer which is configured to acquire a first variation corresponding to a light attenuation variation of a first light beam due to pulsation of blood in a subject, based on a first intensity signal corresponding to an intensity of the first light beam that is transmitted through or reflected from a body of the subject, and that has a first wavelength; a second variation acquirer which is configured to acquire a second variation corresponding to a light attenuation variation of a second light beam due to the pulsation, based on a second intensity signal corresponding to an intensity of the second light beam that is transmitted through or reflected from the body of the subject, and that has a second wavelength; a third variation acquirer which is configured to acquire a third variation corresponding to a light attenuation variation of a third light beam due to the pulsation, based on a third intensity signal corresponding to an intensity of the third light beam that is transmitted through or reflected from the body of the subject, and that has a third wavelength; a concentration calculator which is configured to calculate a blood light absorber concentration in the blood, based on the first variation and the second variation; an estimated value calculator which is configured to calculate an estimated value of the third variation, based on the first variation and the second variation; and an evaluator which is configured to evaluate reliability of a calculated value of the blood light absorber concentration, based on the third variation acquired by the third variation acquirer, and the estimated value calculated by the estimated value calculator.

DETAILED DESCRIPTION OF EXEMPLARY EMBODIMENTS

Figure 1:
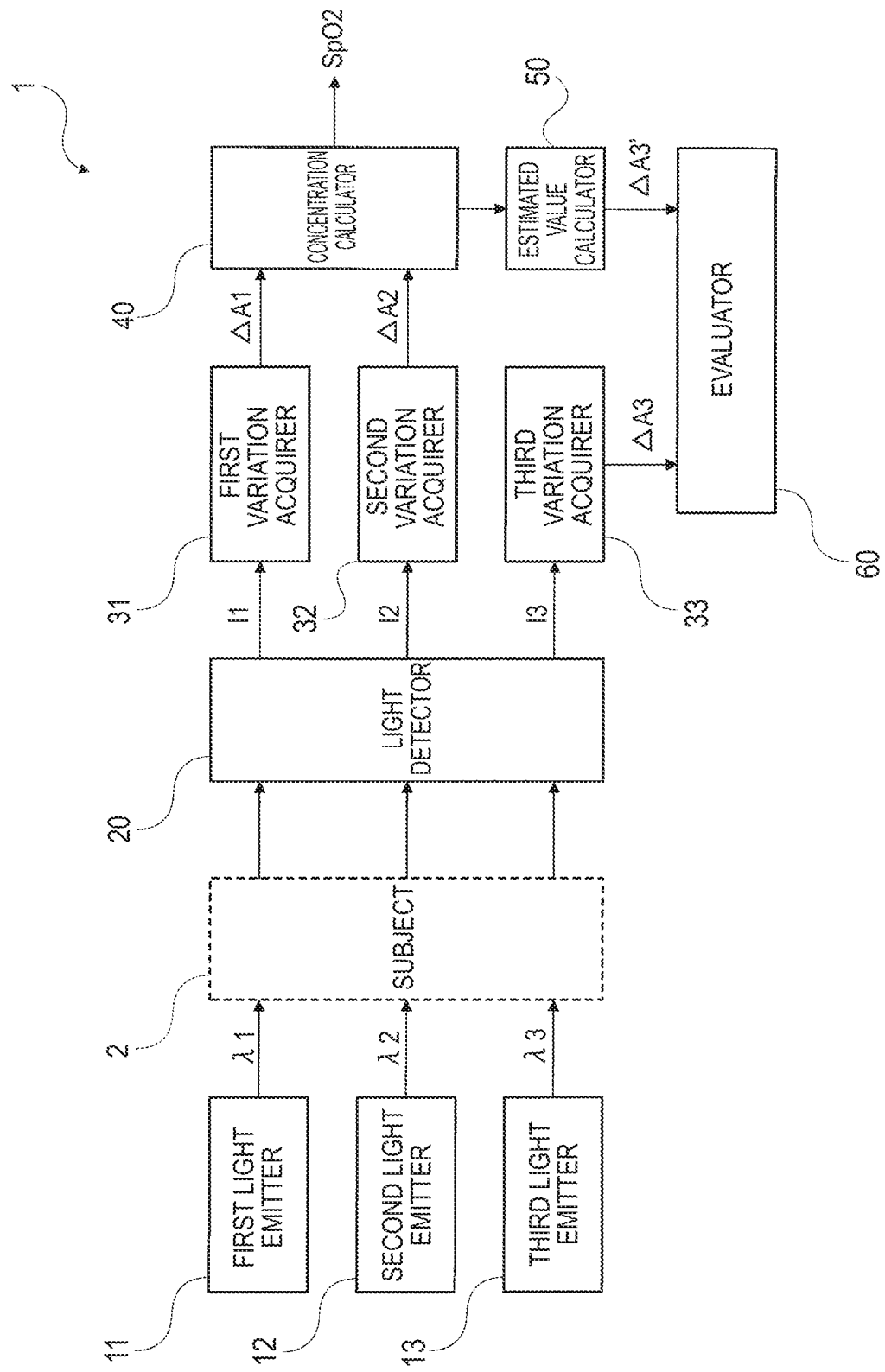
FIG. 1 is a diagram illustrating the functional configuration of a pulse oximeter in a first embodiment.

Hereinafter, embodiments will be described in detail with reference to the accompanying drawings. FIG. 1 is a diagram illustrating the functional configuration of a pulse oximeter (an example of the pulse photometer) in a first embodiment. The pulse oximeter 1 is an apparatus which calculates the SpO2 of a subject 2. The SpO2 indicates a ratio (an example of the blood light absorber concentration) of oxyhemoglobin (an example of the blood light absorber) to the amount of hemoglobin capable of carrying oxygen.

The pulse oximeter may include a first light emitter 11, a second light emitter 12, a third light emitter 13, a light detector 20, a first variation acquirer 31, a second variation acquirer 32, a third variation acquirer 33, a concentration calculator 40, an estimated value calculator 50, and an evaluator 60.

The first light emitter 11 is configured so as to emit a first light beam having a first wavelength λ1. An example of the first wavelength λ1 is 880 nm (an example of the infrared light beam). For example, the first light emitter 11 is a semiconductor light emitting device which can emit the first light beam. Examples of the semiconductor light emitting device are a light emitting diode (LED), a laser diode, and an organic electroluminescence.

The second light emitter 12 is configured so as to emit a second light beam having a second wavelength λ2. Examples of the second wavelength λ2 are 630 nm and 660 nm (examples of the red light beam). For example, the second light emitter 12 is a semiconductor light emitting device which can emit the second light beam. Examples of the semiconductor light emitting device are a light emitting diode (LED), a laser diode, and an organic electroluminescence.

The third light emitter 13 is configured so as to emit a third light beam having a third wavelength λ3. An example of the third wavelength λ3 is 940 nm (an example of the infrared light beam). For example, the third light emitter 13 is a semiconductor light emitting device which can emit the third light beam. Examples of the semiconductor light emitting device are a light emitting diode (LED), a laser diode, and an organic electroluminescence.

The light detector 20 is configured so as to output a first intensity signal I1 in accordance with the intensity of the first light beam transmitted through or reflected from the body of the subject 2. Moreover, the light detector 20 is configured so as to output a second intensity signal I2 in accordance with the intensity of the second light beam transmitted through or reflected from the body of the subject 2. Furthermore, the light detector 20 is configured so as to output a third intensity signal I3 in accordance with the intensity of the third light beam transmitted through or reflected from the body of the subject 2. For example, the light detector 20 is an optical sensor having a sensitivity to the first wavelength λ1, the second wavelength λ2, and the third wavelength λ3. Examples of the optical sensor are a photodiode, a phototransistor, and a photoresistor.

The first light emitter 11, the second light emitter 12, the third light emitter 13, and the light detector 20 are supported by a probe (not shown) which is to be attached to the body of the subject 2. The probe is detachable from the pulse oximeter 1. The configuration of the probe is well known, and therefore its detailed description is omitted.

The first variation acquirer 31 is configured so as to acquire a first variation $\Delta A1$ corresponding to a light attenuation variation of the first light beam due to the blood pulsation of the subject 2 based on a temporal change of the first intensity signal I1 output from the light detector 20. The first variation $\Delta A1$ is expressed by the following expression:

$$\Delta A1 = \ln[I1/(I1-\Delta I1)] \approx \Delta I1/I1 \quad (1)$$

where $\Delta I1$ indicates the variation of the first intensity signal I1 due to the blood pulsation of the subject 2.

The second variation acquirer 32 is configured so as to acquire a second variation $\Delta A2$ corresponding to a light attenuation variation of the second light beam due to the blood pulsation of the subject 2 based on a temporal change of the second intensity signal I2 output from the light detector 20. The second variation $\Delta A2$ is expressed by the following expression:

$$\Delta A2 = \ln[I2/(I2-\Delta I2)] \approx \Delta I2/I2 \quad (2)$$

where $\Delta I2$ indicates the variation of the second intensity signal I2 due to the blood pulsation of the subject 2.

The third variation acquirer 33 is configured so as to acquire a third variation $\Delta A3$ corresponding to a light attenuation variation of the third light beam due to the blood pulsation of the subject 2 based on a temporal change of the third intensity signal I3 output from the light detector 20. The third variation $\Delta A3$ is expressed by the following expression:

$$\Delta A3 = \ln[I3/(I3-\Delta I3)] \approx \Delta I3/I3 \quad (3)$$

where $\Delta I3$ indicates the variation of the third intensity signal I3 due to the blood pulsation of the subject 2.

The concentration calculator 40 is configured so as to calculate the SpO2 of the subject 2 based on the first variation $\Delta A1$ acquired by the first variation acquirer 31, and the second variation $\Delta A2$ acquired by the second variation acquirer 32. Specifically, the concentration calculator is configured so as to perform the following process.

The first variation $\Delta A1$ and the second variation $\Delta A2$ are expressed by the following expressions:

$$\Delta A1 = \Delta Ab1 + \Delta At1 = Eb1Hb\Delta Db + \Sigma t1\Delta Dt \quad (4)$$

$$\Delta A2 = \Delta Ab2 + \Delta At2 = Eb2Hb\Delta Db + \Sigma t2\Delta Dt \quad (5)$$

where E is the extinction coefficient (dl g$^{-1}$cm$^{-1}$), Hb is the hemoglobin concentration of blood (g dl$^{-1}$), Σ indicates the light attenuation rate (cm$^{-1}$), and $\Delta D$ indicates the thickness change (cm) due to the blood pulsation. The suffix "b" means blood, the suffix "t" means the tissue except blood, the suffix "1" means the first light beam, and the suffix "2" means the second light beam.

Expressions (4) and (5) can be deformed in the following manner:

$$\Delta A1 = Eb1Hb\Delta Db + \sum t1\Delta Dt \quad (6)$$
$$= [Eb1 + (\sum t1\Delta Dt)/(Hb\Delta Db)](Hb\Delta Db)$$
$$= (Eb1 + Ex1)(Hb\Delta Db)$$

$$\Delta A2 = Eb2Hb\Delta Db + \sum t2\Delta Dt \quad (7)$$
$$= [Eb2 + (\sum t2\Delta Dt)/(Hb\Delta Db)](Hb\Delta Db)$$
$$= (Eb2 + Ex2)(Hb\Delta Db)$$

where Ex indicates a variable which is replaced with (ΣtΔDt)/(HbΔDb), the suffix "1" means the first light beam, and the suffix "2" means the second light beam.

Expressions (6) and (7) can be deformed in the following manner:

$$Eb1 + Ex1 - \Delta A1/(Hb\Delta Db) = 0 \quad (8)$$

$$Eb2 + Ex2 - \Delta A2/(Hb\Delta Db) = 0 \quad (9)$$

With respect to Expression (9), Eb2 which is the blood extinction coefficient of the second light beam can be approximated by Eb1 which the blood extinction coefficient of the first light beam in the following manner:

$$Eb2 = a2Eb1 + b2 \quad (10)$$

where a and b are constants, the suffix "1" means the first light beam, and the suffix "2" means the second light beam.

Moreover, Ex2 which is the variable of the second light beam can be approximated by Ex1 which is the variable of the first light beam in the following manner:

$$Ex2 = \alpha 2Ex1 + \beta 2 \quad (11)$$

where α and β are constants, the suffix "1" means the first light beam, and the suffix "2" means the second light beam.

Expressions (8) and (9) are rewritten by using Expressions (10) and (11), and the following expressions are obtained:

$$Eb1 + Ex1 - \Delta A1/(Hb\Delta Db) = 0$$

$$Eb1 - \Delta A1/(Hb\Delta Db) = -Ex1 \quad (12)$$

$$(a2Eb1 + b2) + (a2Ex1 + \beta 2) - \Delta A2/(Hb\Delta Db) = 0$$

$$a2Eb1 - \Delta A2/(Hb\Delta Db) = -\alpha 2Ex1 - \beta 2 - b2 \quad (13)$$

When a constant value which is statistically obtained is used as Ex1, and the following matrix expression is calculated, the values of Eb1 and HbΔDb that are variables are obtained.

(Exp. 1)

$$\begin{pmatrix} 1 & -\Delta A1 \\ a2 & -\Delta A2 \end{pmatrix} \begin{pmatrix} Eb1 \\ \dfrac{1}{Hb\Delta Db} \end{pmatrix} = \begin{pmatrix} -Ex1 \\ -\alpha 2 Ex1 - \beta 2 - b2 \end{pmatrix} \quad (14)$$

When the SpO2 which is expressed in a percentage notification is unit-converted to S which is expressed in a decimal notification, Eb1 which is the extinction coefficient of the first light beam is expressed by the following expression:

$$Eb1 = Eo1\,S + Er1(1-S) \quad (15)$$

where Eo is the extinction coefficient of oxyhemoglobin, Er is the extinction coefficient of deoxyhemoglobin, and the suffix "1" means the first light beam. Therefore, the concentration calculator 40 calculates the SpO2 by the following expression:

$$S = (Eb1 - Er1)/(Eo1 - Er1) \quad (16)$$

The estimated value calculator 50 is configured so as to calculate an estimated value $\Delta A3'$ of the third variation $\Delta A3$ corresponding to the light attenuation variation of the third light beam, based on the first variation $\Delta A1$ acquired by the first variation acquirer 31, and the second variation $\Delta A2$ acquired by the second variation acquirer 32. Specifically, the estimated value calculator is configured so as to calculate the following process.

The estimated value $\Delta A3'$ is expressed by the following expression:

$$\Delta A3' = \Delta Ab3 + \Delta At3 = Eb3\,Hb\Delta Db + \Sigma t3\Delta Dt \quad (17)$$

where, as described above, E is the extinction coefficient (dl g$^{-1}$cm$^{-1}$), Hb is the hemoglobin concentration of blood (g dl$^{-1}$), Σ indicates the light attenuation rate (cm$^{-1}$), and ΔD indicates the thickness change (cm) due to the blood pulsation. The suffix "b" means blood, the suffix "t" means the tissue except blood, and the suffix "3" means the third light beam.

Expression (17) can be deformed in the following manner:

$$\begin{aligned} \Delta A3' &= Eb3\,Hb\Delta Db + \sum t3\Delta Dt \\ &= \left[Eb3 + \left(\sum t3\Delta Dt\right)/(Hb\Delta Db)\right](Hb\Delta Db) \\ &= (Eb3 + Ex3)(Hb\Delta Db) \end{aligned} \quad (18)$$

where, as described above, Ex indicates a variable which is replaced with (ΣtΔDt)/(HbΔDb), and the suffix "3" means the third light beam.

With respect to Expression (18), Eb3 which is the blood extinction coefficient of the third light beam can be approximated by Eb1 which is the blood extinction coefficient of the first light beam in the following manner:

$$Eb3 = a3\,Eb1 + b3 \quad (19)$$

where, as described above, a and b are constants, the suffix "1" means the first light beam, and the suffix "3" means the third light beam.

Moreover, Ex3 which is the variable of the third light beam can be approximated by Ex1 which is the variable of the first light beam in the following manner:

$$Ex3 = \alpha 3\,Ex1 + \beta 3 \quad (20)$$

where α and β are constants, the suffix "1" means the first light beam, and the suffix "3" means the third light beam.

Expression (18) is rewritten by using Expressions (19) and (20), and the following expression is obtained:

$$\Delta A3' = [(a3\,Eb1 + b3) + (\alpha 3\,Ex1 + \beta 3)]Hb\Delta Db \quad (21)$$

When the values of Eb1 and HbΔDb which are calculated from Expression (14) by the concentration calculator 40 are substituted into Expression (21), therefore, the estimated value $\Delta A3'$ can be calculated.

The evaluator 60 is configured so as to evaluate the reliability of the SpO2 which is calculated by the concentration calculator 40, based on the third variation $\Delta A3$ acquired by the third variation acquirer 33, and the estimated value $\Delta A3'$ calculated by the estimated value calculator 50.

Specifically, the evaluator 60 calculates a ratio of the third variation $\Delta A3$ to the estimated value $\Delta A3'$. When the value of the ratio is within the range of 0.9 to 1.1, the evaluator evaluates the SpO2 calculated by the concentration calculator 40, as reliable. When the value of the ratio of the third variation $\Delta A3$ to the estimated value $\Delta A3$ is outside the range, the evaluator 60 evaluates the SpO2 calculated by the concentration calculator 40, as unreliable.

It is contemplated that a difference of the estimated value $\Delta A3'$ from an acquired value of the third variation $\Delta A3$ which is based on an actual measurement is caused by inappropriate positioning of the probe, an operation failure of the apparatus, or the like. In the case where the SpO2 calculated by the concentration calculator 40 is evaluated as unreliable, the evaluator 60 performs at least one of a visual notification and an audible notification to the user. The user who receives the notification takes an appropriate countermeasure.

The pulse oximeter 1 in the embodiment is configured so as to be able to calculate the SpO2 by using the first and second variations $\Delta A1$ and $\Delta A2$ which correspond respectively to the light attenuation variations of the first and second light beams due to the pulsation of the subject 2. According to the configuration, while, by using the third light beam which is not essential for calculation of the SpO2, the third variation $\Delta A3$ corresponding to the light attenuation variation of the third light beam due to the pulsation of the subject 2 is acquired based on an actual measured value, a comparison with the estimated value $\Delta A3'$ of the third variation $\Delta A3$ which is obtained based on the first and second variations $\Delta A1$ and $\Delta A2$ that are used in the process of calculating the SpO2 can be performed.

The reliability of the calculated SpO2 can be evaluated dynamically and in real time. Therefore, it is possible to perform evaluation which more conforms to the current status as compared to the configuration where evaluation is conducted by comparison with a group of data that are previously collected. Consequently, the accuracy of reliability evaluation for the calculated SpO2 can be improved.

In the embodiment, an infrared light beam is used as the first light beam for calculating the SpO2, and a red light beam is used as the second light beam. Alternatively, a red light beam may be used as the first light beam, and an infrared light beam may be used as the second light beam. An infrared light beam is used as the third light beam for evaluating the reliability of the SpO2. Alternatively, a red light beam may be used as the third light beam.

The red light beam and the infrared light beam are a combination in which ratios of the blood light absorbances are varied depending on the oxygen saturation, and therefore particularly the accuracy of the calculation for the SpO2 can be improved.

The embodiment is configured so that the common light detector 20 detects the first light beam emitted from the first light emitter 11, the second light beam emitted from the second light emitter 12, and the third light beam emitted from the third light emitter 13. Alternatively, a configuration may be employed where at least one of the light detector for detecting the first light beam, that for detecting the second light beam, and that for detecting the third light beam is independently disposed.

In the embodiment, the functions of the first variation acquirer 31, the second variation acquirer 32, the third variation acquirer 33, the concentration calculator 40, the estimated value calculator 50, and the evaluator 60 are realized from software executed by a cooperation of a processor and memory which are communicably connected to each other. Examples of the processor are a CPU and an MPU. Examples of the memory are a RAM and a ROM. However, at least one of the functions of the first variation acquirer 31, the second variation acquirer 32, the third variation acquirer 33, the concentration calculator 40, the estimated value calculator 50, and the evaluator 60 may be realized by hardware such as circuit devices, or a combination of hardware and software.

Figure 2:
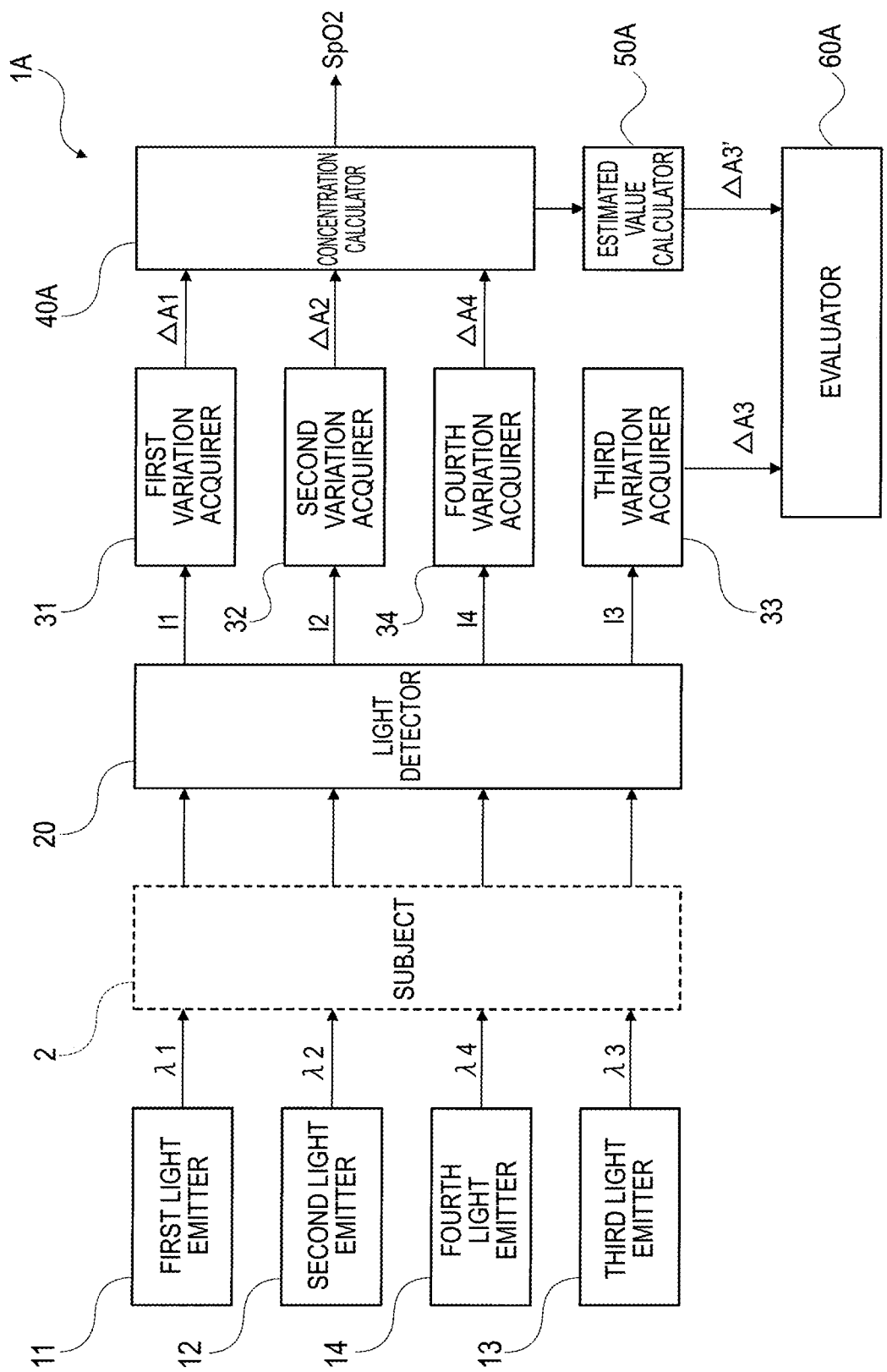
FIG. 2 is a diagram illustrating the functional configuration of a pulse oximeter in a second embodiment.

FIG. 2 is a diagram illustrating the functional configuration of a pulse oximeter 1A in a second embodiment. Portions which are identical or substantially identical with those of the pulse oximeter 1 in the first embodiment are denoted by the same reference numerals, and duplicated descriptions are omitted.

The pulse oximeter 1A may include the first light emitter 11, the second light emitter 12, the third light emitter 13, a fourth light emitter 14, a light detector 20A, the first variation acquirer 31, the second variation acquirer 32, the third variation acquirer 33, a fourth variation acquirer 34, a concentration calculator 40A, an estimated value calculator 50A, and an evaluator 60A.

The fourth light emitter 14 is configured so as to emit a fourth light beam having a fourth wavelength λ4. Examples of the fourth wavelength λ4 are 700 nm (an example of the red light beam), 730 nm (an example of the red light beam), and 805 nm (an example of the infrared light beam). For example, the fourth light emitter 14 is a semiconductor light emitting device which can emit the fourth light beam. Examples of the semiconductor light emitting device are a light emitting diode (LED), a laser diode, and an organic electroluminescence.

The light detector 20A is configured so as to output a fourth intensity signal I4 in accordance with the intensity of the fourth light beam transmitted through or reflected from the body of the subject 2.

The fourth variation acquirer 34 is configured so as to acquire a fourth variation $\Delta A4$ corresponding to a light attenuation variation of the fourth light beam due to the blood pulsation of the subject 2 based on a temporal change of the fourth intensity signal I4 output from the light detector 20A. The fourth variation $\Delta A4$ is expressed by the following expression:

$$\Delta A4 = \ln\ [I4/(I4-\Delta I4)] \approx \Delta I4/I4 \qquad (22)$$

where $\Delta I4$ indicates the variation of the fourth intensity signal I4 due to the blood pulsation of the subject 2.

The concentration calculator 40A is configured so as to calculate the SpO2 of the subject 2 based on the first variation $\Delta A1$ acquired by the first variation acquirer 31, the second variation $\Delta A2$ acquired by the second variation acquirer 32, and the fourth variation $\Delta A4$ acquired by the fourth variation acquirer 34. Specifically, the concentration calculator is configured so as to perform the following process.

The fourth variation $\Delta A4$ is expressed by the following expression:

$$\Delta A4 = \Delta Ab4 + \Delta At4 = Eb4Hb\Delta Db + \Sigma t4\Delta Dt \qquad (23)$$

where, as described above, E is the extinction coefficient (dl g$^{-1}$ cm), Hb is the hemoglobin concentration of blood (g dl$^{-1}$), $\Sigma$ indicates the Light attenuation rate (cm$^{-1}$), and $\Delta D$ indicates the thickness change (cm) due to the blood pulsation. The suffix "b" means blood, the suffix "t" means the tissue except blood, and the suffix "4" means the fourth light beam.

Expression (23) can be deformed in the following manner:

$$\begin{aligned}\Delta A4 &= Eb4Hb\Delta Db + \sum t4\Delta Dt \\ &= [Eb4 + (\sum t4\Delta Dt)/(Hb\Delta Db)](Hb\Delta Db) \\ &= (Eb4 + Ex4)(Hb\Delta Db)\end{aligned} \qquad (24)$$

where, as described above, Ex indicates a variable which is replaced with $(\Sigma t\Delta Dt)/(Hb\Delta Db)$, and the suffix "4" means the fourth light beam.

With respect to Expression (24), Eb4 which is the blood extinction coefficient of the fourth light beam can be approximated by Eb1 which is the blood extinction coefficient of the first light beam in the following manner:

$$Eb4 = a4Eb1 + b4 \qquad (25)$$

where, as described above, a and b are constants, the suffix "1" means the first light beam, and the suffix "4" means the fourth light beam.

Moreover, Ex4 which is the variable of the fourth light beam can be approximated by Ex1 which is the variable of the first light beam in the following manner:

$$Ex4 = \alpha 4Ex1 + \beta 4 \qquad (26)$$

where $\alpha$ and $\beta$ are constants, the suffix "1" means the first light beam, and the suffix "4" means the fourth light beam.

When Expressions (12) and (13) are modified, and Expression (24) is rewritten by using Expressions (25) and (26), the following expressions are obtained:

$$Eb1 + Ex1 - \Delta A1/(Hb\Delta Db) = 0 \qquad (27)$$

$$a2Eb1 + \alpha 2Ex1 - \Delta A2/(Hb\Delta Db) = -b2 - \beta 2 \qquad (28)$$

$$(a4Eb1 + b4) + (\alpha 4Ex1 + \beta 4) - \Delta A4/(Hb\Delta Db) = 0$$

$$a4Eb1 + \alpha 4Ex1 - \Delta A4/(Hb\Delta Db) = -b4 - \beta 4 \qquad (29)$$

In the embodiment, also Ex1 is treated as a variable. When the following matrix expression is calculated, the values of Eb1, Ex1, and Hb$\Delta$Db that are variables are obtained.

(Exp. 2)

$$\begin{pmatrix} 1 & 1 & -\Delta A1 \\ a2 & \alpha 2 & -\Delta A2 \\ a4 & \alpha 4 & -\Delta A4 \end{pmatrix} \begin{pmatrix} Eb1 \\ Ex1 \\ \dfrac{1}{Hb\Delta Db} \end{pmatrix} = \begin{pmatrix} 0 \\ -b2 - \beta 2 \\ -b4 - \beta 4 \end{pmatrix} \qquad (30)$$

The concentration calculator 40A calculates the SpO2 by substituting Eb1 which is the acquired extinction coefficient of the first light beam into Expression (16).

The estimated value calculator 50A is configured so as to calculate an estimated value $\Delta A3'$ of the third variation $\Delta A3$ corresponding to the light attenuation variation of the third light beam, based on the first variation $\Delta A1$ acquired by the first variation acquirer 31, the second variation $\Delta A2$ acquired by the second variation acquirer 32, and the fourth variation $\Delta A4$ acquired by the fourth variation acquirer 34.

Specifically, the values of Eb1,Ex1, and Hb$\Delta$Db which are calculated from Expression (30) by the concentration calculator 40A are substituted into Expression (21), thereby calculating the estimated value $\Delta A3'$.

The evaluator 60A is configured so as to evaluate the reliability of the SpO2 which is calculated by the concentration calculator 40A, based on the third variation $\Delta A3$ acquired by the third variation acquirer 33, and the estimated value $\Delta A3'$ calculated by the estimated value calculator 50A.

Specifically, the evaluator 60A calculates a ratio of the third variation $\Delta A3$ to the estimated value $\Delta A3'$. When the value of the ratio is within the range of 0.9 to 1.1, the evaluator 60A evaluates the SpO2 calculated by the concentration calculator 40A, as reliable. When the value of the ratio of the third variation $\Delta A3$ to the estimated value $\Delta A3'$ is outside the range, the evaluator 60A evaluates the SpO2 calculated by the concentration calculator 40A, as unreliable.

In the case where the SpO2 calculated by the concentration calculator 40A is evaluated as unreliable, the evaluator 60A performs at least one of a visual notification and an audible notification to the user. The user who receives the notification takes an appropriate countermeasure.

The pulse oximeter 1A in the embodiment is configured so as to be able to calculate the SpO2 by using the first, second, and fourth variations $\Delta A1$, $\Delta A2$, and $\Delta A4$ which correspond respectively to the light attenuation variations of the first, second, and fourth light beams due to the pulsation of the subject 2. According to the configuration, while, by using the third light beam which is not essential for calculation of the SpO2, the third variation $\Delta A3$ corresponding to the light attenuation variation of the third light beam due to the pulsation of the subject 2 is acquired based on an actual measured value, a comparison with the estimated value $\Delta A3'$ of the third variation $\Delta A3$ which is obtained based on the first, second, and fourth variations $\Delta A1$, $\Delta A2$, and $\Delta A4$ that are used in the process of calculating the SpO2 can be performed.

The reliability of the calculated SpO2 can be evaluated dynamically and in real time. Therefore, it is possible to perform evaluation which more conforms to the current status as compared to the configuration where evaluation is conducted by comparison with a group of data that are previously collected. Particularly, the SpO2 is calculated by using three wavelengths, and therefore all of the three variables which are necessary for calculating the estimated value $\Delta A3'$ can be acquired based on actual measured values. Consequently, the accuracy of reliability evaluation for the calculated SpO2 can be further improved.

In the embodiment, an infrared light beam is used as the first light beam for calculating the SpO2, and a red light beam is used as the second light beam. Alternatively, a red light beam may be used as the first light beam, and an infrared light beam may be used as the second light beam. An infrared light beam is used as the third light beam for evaluating the reliability of the SpO2. Alternatively, a red light beam may be used as the third light beam.

The red light beam and the infrared light beam are a combination in which ratios of the blood light absorbances are varied depending on the oxygen saturation, and therefore particularly the accuracy of the calculation for the SpO2 can be improved.

The embodiment is configured so that the common light detector 20A detects the first light beam emitted from the first light emitter 11, the second light beam emitted from the second light emitter 12, the third light beam emitted from the third light emitter 13, and the fourth light beam emitted from the fourth light emitter 14. Alternatively, a configuration may be employed where at least one of the light detector for detecting the first light beam, that for detecting the second light beam, that for detecting the third light beam, and that for detecting the fourth light beam is independently disposed.

In the embodiment, the functions of the first variation acquirer 31, the second variation acquirer 32, the third variation acquirer 33, the fourth variation acquirer 34, the concentration calculator 40A, the estimated value calculator 50A, and the evaluator 60A are realized from software executed by a cooperation of a processor and memory which are communicably connected to each other. Examples of the processor are a CPU and an MPU. Examples of the memory are a RAM and a ROM. However, at least one of the functions of the first variation acquirer 31, the second variation acquirer 32, the third variation acquirer 33, the fourth variation acquirer 34, the concentration calculator 40A, the estimated value calculator 50A, and the evaluator 60A may be realized by hardware such as circuit devices, or a combination of hardware and software.

The above-described embodiments are mere examples for facilitating understanding of the presently disclosed subject matter. The configurations in the embodiments may be adequately changed or improved without departing from the spirit of the presently disclosed subject matter. It is obvious that equivalents are included within the technical scope of the presently disclosed subject matter.

In the above-described embodiments, a pulse oximeter for calculating the SpO2 has been exemplified. However, the presently disclosed subject matter can be applied also to other kinds of pulse photometers which measure the concentration of another blood light absorber. Examples of another blood light absorber are carboxyhemoglobin, methemoglobin, and a dye injected into blood vessels. In this case, the wavelengths of the light beams are selected so that combinations can be produced in which ratios of the blood light absorbances are substantially different from each other depending on the target blood light absorber concentration. In a pulse photometer for calculating a plurality of kinds of blood light absorbers, a light beam which is to be used for reliability evaluation, and which is not essential for calculating the concentration of one of the blood light absorbances may be used for calculating the concentration of the other blood light absorber.

A configuration may be employed where four or more light beams at four or more wavelengths are used for calculating the blood light absorber concentration. According to the configuration, the reliability of a calculated blood light absorber concentration can be evaluated by using a fifth light beam which is not essential for calculating the blood light absorber concentration. For example, five wavelengths $\lambda 1$, $\lambda 2$, $\lambda 3$, $\lambda 4$, and $\lambda 5$ may be selected as follows:

$\lambda 1$=630 nm, $\lambda 2$=660 nm, $\lambda 3$=700 nm, $\lambda 4$=880 nm, $\lambda 5$=940 nm; or $\lambda 1$=660 nm, $\lambda 2$=700 nm, $\lambda 3$=730 nm, $\lambda 4$=880 nm, $\lambda 5$=940 nm.

In the above-described embodiments, pulse oximeters have been exemplified as pulse photometers. The term "pulse photometer" used in the specification includes a patient monitor, defibrillator, medical transmitter, and the like which have a function of calculating the SpO2.

According to an aspect of the presently disclosed subject matter, the pulse photometer is configured so as to be able to calculate the blood light absorber concentration by using the first and second variations which correspond respectively to the light attenuation variations of the first and second light beams due to the pulsation of the subject. According to t configuration, while, by using the third light beam which is not essential for calculation of the blood light absorber concentration, the third variation corresponding to the light attenuation variation of the third light due to the pulsation of the subject is acquired based on an actual measured value, a comparison with the estimated value of the third variation which is obtained based on the first and second variations that are used in the process of calculating the blood light absorber concentration can be performed.

The reliability of the calculated blood light absorber concentration can be evaluated dynamically and in real time. Therefore, it is possible to perform evaluation which more conforms to the current status as compared to the configuration where evaluation is conducted by comparison with a group of data that are previously collected. Consequently, the accuracy of reliability evaluation for the calculated blood light absorber concentration can be improved.

What is claimed is:

1. A pulse photometer comprising:
   a first light emitter configured to emit a first light beam having a first wavelength;
   a second light emitter configured to emit a second light beam having a second wavelength;
   a third light emitter configured to emit a third light beam having a third wavelength;
   a light detector configured to output a first intensity signal in accordance with an intensity of the first light beam that is transmitted through or reflected from a body of a subject, a second intensity signal in accordance with an intensity of the second light beam that is transmitted through or reflected from the body of the subject, and a third intensity signal in accordance with an intensity of the third light beam that is transmitted through or reflected from the body of the subject;
   a memory storing computer-readable instructions; and
   a processor configured to execute the computer-readable instructions, which when executed cause the processor to control the pulse photometer to:
   acquire a first variation corresponding to a light attenuation variation of the first light beam due to pulsation of blood in the subject, based on the first intensity signal;
   acquire a second variation corresponding to a light attenuation variation of the second light beam due to the pulsation, based on the second intensity signal;
   acquire a third variation corresponding to a light attenuation variation of the third light beam due to the pulsation, based on the third intensity signal;
   calculate a blood light absorber concentration in the blood, based on the first variation and the second variation;
   calculate an estimated value of the third variation, based on the first variation and the second variation;
   determine whether the blood light absorber concentration in the blood is a reliable measurement of the pulse photometer, based on the third variation and the estimated value of the third variation; and
   output, to a user of the pulse photometer, an indication when the determination identifies that the blood light absorber concentration in the blood is an unreliable measurement.

2. The pulse photometer according to claim 1, wherein one of the first light beam and the second light beam is a red light beam, and the other of the first light beam and the second light beam is an infrared light beam.

3. The pulse photometer according to claim 1, further comprising:
   a fourth light emitter,
   wherein the fourth light emitter is configured to emit a fourth light beam having a fourth wavelength, the light detector is configured to output a fourth intensity signal in accordance with an intensity of the fourth light beam that is transmitted through or reflected from the body of the subject, and
   wherein the processor, when the computer-readable instructions are executed, controls the pulse photometer to acquire a fourth variation corresponding to a light attenuation variation of the fourth light beam due to the pulsation, based on the fourth intensity signal, calculate the blood light absorber concentration based on the first variation, the second variation, and the fourth variation, and calculate the estimated value of the third variation based on the first variation, the second variation, and the fourth variation.

4. The pulse photometer according to claim 3, wherein the first wavelength, the second wavelength, the third wavelength, and the fourth wavelength are selected from 630 nm, 660 nm, 700 nm, 730 nm, 805 nm, 880 nm, and 940 nm.

5. The pulse photometer according to claim 1, wherein the processor controls the pulse photometer to calculate a ratio between the third variation and the estimated value of the third variation and to determine that the ratio between the third variation and the estimated value is outside a range of the ratio between the third variation and the estimated value, the range indicating the blood light absorber concentration in the blood is a reliable measurement of the pulse photometer.

6. The pulse photometer according to claim 1, wherein the indication comprises at least one of an audio notification and a visual notification.

7. A pulse photometer comprising:
   a memory storing computer-readable instructions; and
   a processor configured to execute the computer-readable instructions, which when executed cause the processor to control the pulse photometer to:
   acquire a first variation corresponding to a light attenuation variation of a first light beam due to pulsation of blood in a subject, based on a first intensity signal corresponding to an intensity of the first light beam that is transmitted through or reflected from a body of the subject, and that has a first wavelength;
   acquire a second variation corresponding to a light attenuation variation of a second light beam due to the pulsation, based on a second intensity signal corresponding to an intensity of the second light beam that is transmitted through or reflected from the body of the subject, and that has a second wavelength;
   acquire a third variation corresponding to a light attenuation variation of a third light beam due to the pulsation, based on a third intensity signal corresponding to an intensity of the third light beam that is transmitted through or reflected from the body of the subject, and that has a third wavelength;

calculate a blood light absorber concentration in the blood, based on the first variation and the second variation;

calculate an estimated value of the third variation, based on the first variation and the second variation;

determine whether the blood light absorber concentration in the blood is a reliable measurement of the pulse photometer, based on the third variation and the estimated value of the third variation; and output, to a user of the pulse photometer, an indication when the determination identifies that the blood light absorber concentration in the blood is an unreliable measurement.

8. The pulse photometer according to claim 7, wherein the processor, when the computer-readable instructions are executed, controls the pulse photometer to acquire a fourth variation corresponding to a light attenuation variation of a fourth light beam due to the pulsation, based on a fourth intensity signal corresponding to an intensity of the fourth light beam that is transmitted through or reflected from the body of the subject, and that has a fourth wavelength, calculate the blood light absorber concentration based on the first variation, the second variation, and the fourth variation, and calculate the estimated value of the third variation based on the first variation, the second variation, and the fourth variation.

9. The pulse photometer according to claim 7, wherein the processor controls the pulse photometer to calculate a ratio between the third variation and the estimated value of the third variation and to determine that the ratio between the third variation and the estimated value is outside a range of the ratio between the third variation and the estimated value, the range indicating the blood light absorber concentration in the blood is a reliable measurement of the pulse photometer.

10. The pulse photometer according to claim 7, wherein the indication comprises at least one of an audio notification and a visual notification.

11. A method for evaluating reliability of a calculated value of a blood light absorber concentration, the method comprising:

causing a pulse photometer to acquire a first variation corresponding to a light attenuation variation of a first light beam due to pulsation of blood in a subject, based on a first intensity signal corresponding to an intensity of the first light beam that is transmitted through or reflected from a body of the subject, and that has a first wavelength;

causing the pulse photometer to acquire a second variation corresponding to a light attenuation variation of a second light beam due to the pulsation, based on a second intensity signal corresponding to an intensity of the second light beam that is transmitted through or reflected from the body of the subject, and that has a second wavelength;

causing the pulse photometer to acquire a third variation corresponding to a light attenuation variation of a third light beam due to the pulsation, based on a third intensity signal corresponding to an intensity of the third light beam that is transmitted through or reflected from the body of the subject, and that has a third wavelength;

causing the pulse photometer to calculate a blood light absorber concentration in the blood, based on the first variation and the second variation;

causing the pulse photometer to calculate an estimated value of the third variation, based on the first variation and the second variation;

causing the pulse photometer to determine whether the blood light absorber concentration in the blood is a reliable measurement of the pulse photometer, based on the third variation and the estimated value of the third variation; and causing the pulse photometer to output, to a user of the pulse photometer, an indication when the determination identifies that the blood light absorber concentration in the blood is an unreliable measurement.

12. The method according to claim 11, wherein one of the first light beam and the second light beam is a red light beam, and the other of the first light beam and the second light beam is an infrared light beam.

13. The method according to claim 11, further comprising:

causing the pulse photometer to acquire a fourth variation corresponding to a light attenuation variation of a fourth light beam due to the pulsation, based on a fourth intensity signal corresponding to an intensity of the fourth light beam that is transmitted through or reflected from the body of the subject, and that has a fourth wavelength, wherein the blood light absorber concentration is calculated based on the first variation, the second variation, and the fourth variation, and the estimated value of the third variation is calculated based on the first variation, the second variation, and the fourth variation.

14. The method according to claim 13, wherein the first wavelength, the second wavelength, the third wavelength, and the fourth wavelength are selected from 630 nm, 660 nm, 700 nm, 730 nm, 805 nm, 880 nm, and 940 nm.

15. The method according to claim 11, further comprising:

causing the pulse photometer to calculate a ratio between the third variation and the estimated value of the third variation; and causing the pulse photometer to determine that the ratio between the third variation and the estimated value is outside a range of the ratio between the third variation and the estimated value, the range indicating the blood light absorber concentration in the blood is a reliable measurement of the pulse photometer.

16. The method according to claim 11, wherein the indication comprises at least one of an audio notification and a visual notification.

* * * * *